(12) United States Patent
Wu et al.

(10) Patent No.: US 11,357,234 B2
(45) Date of Patent: Jun. 14, 2022

(54) FOOD SAFETY QUALITY AND PERFORMANCE MONITORING SYSTEM AND METHOD THEREOF

(71) Applicant: Yuan Jin Chuang Enterprise Co.,Ltd, New Taipei (TW)

(72) Inventors: Hung-Yuan Wu, Yunlin County (TW); Meng-Hui Lin, Yunlin County (TW)

(73) Assignee: Yuan Jin Chuang Enterprise Co., Ltd, New Taipei (TW)

( * ) Notice: Subject to any disclaimer, the term of this patent is extended or adjusted under 35 U.S.C. 154(b) by 784 days.

(21) Appl. No.: 16/283,691

(22) Filed: Feb. 22, 2019

(65) Prior Publication Data

US 2020/0170264 A1 Jun. 4, 2020

(30) Foreign Application Priority Data

Dec. 3, 2018 (TW) .................................. 107143229

(51) Int. Cl.
*A22B 5/00* (2006.01)
*G01N 33/12* (2006.01)

(52) U.S. Cl.
CPC ............... *A22B 5/00* (2013.01); *G01N 33/12* (2013.01)

(58) Field of Classification Search
CPC .................................. A22B 5/00; G01N 33/12
See application file for complete search history.

(56) References Cited

U.S. PATENT DOCUMENTS 6,985,779 B2    1/2006  Hsiung et al.
2018/0321667 A1 11/2018 Cella et al.

FOREIGN PATENT DOCUMENTS

TW          200807205          2/2008

*Primary Examiner* — Anthony Ho
(74) *Attorney, Agent, or Firm* — JCIP Global Inc.

(57) ABSTRACT

A food safety quality and performance monitoring system is provided, which is part of Industry 4.0 factory monitoring, including: a slaughter production line monitoring module recording a first monitoring information including quantity, voltage, temperature and humidity, time, and the like; a processing line monitoring module recording a second monitoring information including quantity, temperature and humidity, time, metal detection, and the like; an intelligent central monitoring server storing the first monitoring information and the second monitoring information and allowing a user to register and log in; and a human-machine interface facilitating the security and performance monitoring of the food production line. A food safety quality and performance monitoring method is further provided.

14 Claims, 5 Drawing Sheets

FOOD SAFETY QUALITY AND PERFORMANCE MONITORING SYSTEM AND METHOD THEREOF

CROSS-REFERENCE TO RELATED APPLICATION

This application claims the priority benefit of Taiwan application serial no. 107143229, filed on Dec. 3, 2018. The entirety of the above-mentioned patent application is hereby incorporated by reference herein and made a part of this specification.

BACKGROUND OF THE INVENTION

Field of the Invention

The invention relates to a monitoring system and method thereof, and more particularly, to a monitoring system and method thereof for food safety quality and performance.

Description of Related Art

With the development of animal husbandry, the concept of saving labor costs has gradually received the attention of the industry. To improve the quality of the poultry industry, it is necessary to integrate multiple projects controlled by the aquaculture environment, and then data of each batch of poultry from breeding/incubation, breeding, slaughtering, processing, and sales, and the like is categorized and collected to achieve the objective of establishing a production resume. As far as poultry meat processing is concerned, the awareness of food safety among the people is on the rise. When consumers purchase food or ingredients in the supermarket or traditional market, sellers are required to have national quarantine certification or clearly mark the ingredients of food such that consumers may determine the safety of food during purchase. Moreover, the techniques of food production and processing today are more and more diverse and complex, where the food on the market needs to be processed, preserved, quarantined, and transported from harvest production to sales. Each process is strictly controlled to ensure the freshness and safety of food.

However, as far as the food safety is concerned, the average consumer often may only know the status of the purchased item and evaluate the purchased item through the third-party inspection report provided by the terminal seller, and cannot further understand the complete production history of the purchased item, and the process of tracing the food history is quite cumbersome and time consuming. From the production end, the processing plant end, the logistics end to the consumer end, it takes a lot of human resources and working time, and each inspection step must be thoroughly done in order to proceed to the next step. Moreover, it is difficult to effectively carry out centrally managed integrated control on various production lines for slaughtering and processing. Therefore, it is necessary to propose a system that may completely record all the history and display abnormal warnings in real time, which may automatically collect complete production records on slaughtering and processing steps and be transparent regarding food safety information for consumers, and may promptly issue an alert when an abnormality occurs. Abnormality processing may be further performed via the production line site or central monitoring to reduce and prevent production losses to achieve the objective of maintaining consumer food safety and improve the productivity of the industry.

SUMMARY OF THE INVENTION

In view of the above shortcomings of the prior art, a main objective of the invention is to provide a food safety quality and performance monitoring system capable of automatically collecting complete production records relating to slaughtering and processing steps, and be transparent regarding food safety information for consumers, and may promptly issue an alert when an abnormality occurs. Abnormality processing may be further performed via the production line site or central monitoring to reduce and prevent production losses to achieve the objective of maintaining consumer food safety and improve the productivity of the industry.

In order to achieve the foregoing and other objectives, the invention provides a food safety quality and performance monitoring system, including: a slaughter line monitoring module configured for generating a first monitoring information and including a first human-machine controller, at least one first quantity recording unit, at least one voltage recording unit, at least one first temperature and humidity recording unit, at least one first time recording unit, and at least one first barcode scanning unit; wherein the first human-machine controller is configured to input a slaughter line instruction and is respectively connected to the at least one first quantity recording unit, the at least one voltage recording unit, the at least one first temperature and humidity recording unit, the at least one first time recording unit, and the at least one first barcode scanning unit; a processing line monitoring module is configured for generating a second monitoring information and connected to the slaughter line monitoring module, the processing line monitoring module includes a second human-machine controller, at least one second quantity recording unit, at least one second temperature and humidity recording unit, at least one second time recording unit, at least one metal detecting unit, and at least one second barcode scanning unit; wherein the second human-machine controller is configured to input a processing line instruction and is respectively connected to the at least one second quantity recording unit, the at least one voltage recording unit, the at least one second temperature and humidity recording unit, the at least one second time recording unit, and the at least one second barcode scanning unit; an intelligent central monitoring server is connected to the slaughter line monitoring module and the processing line monitoring module and configured to respectively store the first monitoring information and the second monitoring information; the intelligent central monitoring server includes a registration module, a login module, a HACCP module, wherein the registration module is configured to allow at least one user to store at least one personal information; the login module is configured to allow the at least one user to access the first monitoring information, the second monitoring information, and the HACCP module according to the at least one personal information; and a human-machine interface is connected to the slaughter line monitoring module, the processing line monitoring module, and the intelligent central monitoring server to receive the first monitoring information and the second monitoring information, and when the human-machine interface determines that at least one of the first monitoring information and the second monitoring information is abnormal, a central monitoring instruction is transmitted to the abnormal slaughter line monitoring module or the processing line monitoring module.

When the food safety quality and performance monitoring system of the invention is started, the first monitoring information is recorded via the slaughter line monitoring module, wherein the first monitoring information includes: at least one first quantity information generated by the at least one first quantity unit, at least one voltage recording information generated by the at least one voltage recording unit, at least one first temperature and humidity information generated by the at least one first temperature and humidity recording unit, at least one first time information generated by the at least one first time recording unit, at least one first barcode information generated by the at least one first barcode scanning unit, and the first human-machine controller displays at least one of the first quantity information, the at least one voltage recording information, the at least one first temperature and humidity information, the at least one first time information, and the at least one first barcode information; next, the second monitoring information is recorded via the processing line monitoring module, the second monitoring information including: at least one second quantity information generated by the at least one second quantity recording unit, at least one second temperature and humidity information generated by the at least one second temperature and humidity recording unit, at least one second time information generated by the at least one second time recording unit, at least one metal detection information generated by the at least one metal detecting unit, and at least one second barcode information generated by the at least one second barcode scanning unit; then, after the intelligent central monitoring server respectively stores the first monitoring information and the second monitoring information, the registration module stores the at least one personal information of the at least one user in a manner of allowing the at least one user to perform a registration step; finally, the at least one user who has completed the registration step may use the login module to allow the at least one user to access the first monitoring information, the second monitoring information, and the HACCP data and food factory quality monitoring module according to the at least one personal information; in addition, when the human-machine interface determines that at least one of the first monitoring information and the second monitoring information is abnormal, the human-machine interface may transmit a central monitoring instruction to the slaughter line monitoring module and the processing line monitoring module.

In this way, both the slaughter line and the processing line have their own independent and automatic operation of a plurality of monitoring modules, which may make important information of a plurality of monitoring and control points including time, temperature and humidity, quantity, etc. in the production process to be automatically recorded, and the first human-machine controller and the second human-machine controller may instantly display the current state and achieve warning function to prevent problematic products from reaching the production backend or even the consumer; moreover, in the later stage, whether there is any doubt in the slaughtering or processing flow on the production line, the owner or the at least one user may further learn all relevant information about food safety quality via the intelligent central monitoring server storing the first monitoring information and the second monitoring information, and the owner may also further learn whether the performance on the production process is low or abnormal respectively via the first monitoring information displayed via the first human-machine controller on the slaughter line and the second monitoring information displayed via the second human-machine controller on the processing line, and the human-machine interface in the backend may issue the central monitoring instruction to effectively perform central management type of coordinated control to perform abnormal processing to reduce and prevent production losses to achieve the objectives of maintaining consumer food safety and improving the production efficiency of the industry.

More specifically, a webpage module further includes a database and a processing unit; each of the at least one voltage recording unit is a voltmeter disposed in a corona machine; and the at least one personal information is used as a combination of a market product demand analysis and an evaluation of a production usage.

More specifically, each of the at least one first quantity recording unit is a counter disposed in a hanging machine; and each of the at least one second quantity recording unit is a counter disposed in one of a check area and a vacuum packaging area.

More specifically, each of the at least one first temperature and humidity recording unit is a temperature and humidity meter disposed in one of a scalding machine, a glue applicator, and a cooling tank; and each of the at least one second temperature and humidity recording unit is a temperature and humidity meter disposed in one of a freezer, a rapid freezer, a braised pot, a cooling tank, a sterilization tank, and an ice water tank.

More specifically, each of the at least one first time recording unit is a timer disposed in one of a corona machine, a scalding machine, a hair removal machine, and a cooling tank; and each of the at least one second time recording unit is a timer disposed in one of a sterilization tank, a cold water tank, and a rapid freezer.

Further, each of the at least one first time recording unit is configured with at least one temperature sensor and a humidity sensor in the production working environment, and the automatic control rule of the intelligent central monitoring server instantly issues an instruction to the on-site thermostat for intelligent regulation, and a central monitoring instruction may also be issued via the human-machine interface in the backend to effectively perform remote control.

In view of the disadvantages of the prior art previously described, another objective of the invention is to provide a food safety quality and performance monitoring method, including the following steps. A first monitoring information is recorded via a slaughter line monitoring module, the first monitoring information including: at least one first quantity information, at least one voltage recording information, at least one first temperature and humidity information, at least one first time information, and at least one first barcode information; and a first human-machine controller configured to input a slaughter line instruction and simultaneously display at least one of the at least one first quantity information, the at least one voltage recording information, the at least one first temperature and humidity information, the at least one first time information, and the at least one first barcode information. A second monitoring information is recorded via a processing line monitoring module, the second monitoring information including: at least one second quantity information, at least one second temperature and humidity information, at least one second time information, at least one metal detection information, and at least one second barcode information; and a second human-machine controller configured to input a processing line instruction and simultaneously display at least one of the at least one second quantity information, the at least one second temperature and humidity information, the at least one second time information, the at least one metal detection information, and the at least one second barcode information. A first monitoring information generated by the slaughter line monitoring module and a second monitoring information generated by the processing line monitoring module are respectively recorded via an intelligent central monitoring server. At least one personal information of at least one user is stored via a registration module included in the intelligent central monitoring server. A login module included in the intelligent central monitoring server allows the at least one user to access the first monitoring information, the second monitoring information, and an HACCP data and food factory quality monitoring module included in webpage information according to the at least one personal information. A central monitoring instruction is transmitted to the slaughter line monitoring module and the processing line monitoring module when at least one of the first monitoring information and the second monitoring information is determined to be abnormal.

More specifically, the intelligent central monitoring server further includes a database and a processing unit; and each of at least one voltage recording unit for recording the at least one voltage information is a voltmeter disposed in a corona machine.

More specifically, each of at least one first quantity recording unit for recording the at least one first quantity information is a counter disposed in a hanging machine; and each of at least one second quantity recording unit for recording the at least one second quantity is a counter disposed in one of a check area and a vacuum packaging area.

More specifically, each of at least one first temperature and humidity recording unit for recording the at least one first temperature and humidity information is a temperature and humidity meter disposed in one of a scalding machine, a glue applicator, and a cooling tank; and each of at least one second temperature and humidity recording unit for recording the at least one second temperature and humidity information is a temperature and humidity meter disposed in one of a freezer, a rapid freezer, a braised pot, a cooling tank, a sterilization tank, and an ice water tank.

Further, each of the at least one time recording unit for recording the at least one first time information is a timer disposed in one of a corona machine, a scalding machine, a hair removal machine, and a cooling tank. Each of the at least one second time recording unit is a timer disposed in one of a sterilization tank, a cold water tank, and a rapid freezer, and is automatically stored in a database via a processing unit, and personnel may query a history trend graph or tabular data via the human-machine interface which may also be exported as electronic data files, such as EXCEL, Access, etc, wherein each of the plurality of analysis materials is configured for exporting to at least one of a video wall, a desktop computer, a notebook computer, a car computer, a personal digital assistant, a tablet computer, a smart phone, a digital photo frame, and a wearable device to be read.

More specifically, the intelligent central monitoring server further receives an access control card information to obtain the immediate number of workers of each working area according to the access control card information and statistically calculate monthly working hours and a production status of each of the working areas.

More specifically, the intelligent central monitoring server further generates a history barcode to be scanned by the at least one first barcode scanning unit and the at least one second barcode scanning unit to perform batch management.

More specifically, the intelligent central monitoring server automatically debugs the central monitoring instruction via a preset rule to exclude an abnormality of the slaughter line monitoring module or the processing line monitoring module.

More specifically, the intelligent central monitoring server further counts the abnormality of the history and draws a curve according to the abnormality of the history, when a fluctuation of the curve is greater than a preset condition, the intelligent central monitoring server analyzes an auxiliary quality determination information.

Further, each intelligent central monitoring server includes a processing unit, and when the first human-machine controller or the second human-machine controller receives an on-site value exceeding a preset alarm limit value, the automatic control rule of the processing unit in the human-machine interface sends at least one email message to the designated recipient's email mailbox for alarm notification. For example, the upper limit temperature for the set alarm limit value is 10 degrees, and when the on-site measured environment or equipment temperature exceeds 10 degrees, the intelligent central monitoring server sends an email message to the designated recipient's email address, and the human-machine interface also instantly displays information such as the alarm occurrence time, alarm monitoring point, and processing status. The above examples are merely for the brief description of the operation method of the intelligent central monitoring server and are not necessary limitations of the invention.

Further, each first human-machine controller or second human-machine controller is electrically connected to at least one electronic scale via a communication line of RS-232 or RS485 or Ethernet, and when the on-site operator does the weighing, the first human-machine controller or the second human-machine controller automatically accepts the weight of the electronic scale, and level classification is performed by the internal automatic control rule, and at the same time the measured value is transmitted to the intelligent central monitoring server and is then recorded to the database via the processing unit.

Further, an access control card swiping device is installed in a specific operation area of each plant area, and the personnel all need to swipe the card to open and exit the at least one work area, and the human-machine interface is electrically connected to at least one card swiping device via a communication line of RS-232 or RS485 or Ethernet. The cardholder's card swiping time is recorded when the card is swiped, which is recorded to the database via the processing unit in the human-machine interface, and the working time and the total number of employees are automatically calculated and then converted into average working hours.

Further, the intelligent central monitoring server has a production history tracing function, and the intelligent central monitoring server is connected to at least one ERP database, and the personnel inputs a product production number such as a batch number in the human-machine interface, and the intelligent central monitoring server may search for the source information of the product, such as a source farm name, a purchase quantity, a production quantity, etc. The above examples are only for the brief description of the operation method of the intelligent central monitoring server, and are not necessary limits of the invention. This feature may be used as a food safety and prevention management.

Further, each first human-machine controller or second human-machine controller is electrically connected to at least one food-grade metal detecting device via a communication line of RS-232 or RS485 or Ethernet. When the metal detecting device operates, the first human-machine controller or the second human-machine controller automatically receives the normal and abnormal quantity data detected by the metal detecting device, and the value is sent to the intelligent central monitoring server via the first human-machine controller or the second human-machine controller and then recorded to the database via the processing unit.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

In the following, specific embodiments are used to describe the implementation of the invention. Those skilled in the art may better understand the other advantages and efficacy of the invention from the contents disclosed in the specification. The invention may also be implemented or applied through other different specific embodiments, and the details of the specification of the invention may also be modified and changed based on different views and applications without departing from the spirit of the invention.

It is to be understood that the structure, the proportion, the size, the number of components, and the like in the drawings of the specification are only used to match the contents disclosed in the specification for understanding and reading by those skilled in the art, and are not intended to limit the feasible limiting conditions of the invention. Therefore, the above are not technically meaningful, and any modification of the structure, change of the proportional relationship, or adjustment of the size shall fall within the scope applicable to the technical contents disclosed in the invention without affecting the resulting effects and the achievable objectives of the invention.

Referring to FIG. 1 to FIG. 4, schematics of the architecture of the food safety quality and performance monitoring system of the invention are provided.

Hereinafter, in accordance with an embodiment of the invention, a food safety quality and performance monitoring system 1 is described, including: a slaughter line monitoring module 10, a processing line monitoring module 20, an intelligent central monitoring server 30, and a human-machine interface 40.

The slaughter line monitoring module 10 includes a first human-machine controller 11, a first quantity recording unit 12, a voltage recording unit 13, a first temperature and humidity recording unit 14, a first time recording unit 15, and a first code scanning unit 16, wherein the first human-machine controller 11 is configured to input a slaughter line instruction (not shown) and is respectively connected to the first quantity recording unit 12, the voltage recording unit 13, the first temperature and humidity recording unit 14, the first time recording unit 15, and the first code scanning unit 16. In an embodiment of the invention, the slaughter line monitoring module 10 records a first monitoring information 100. The first monitoring information 100 includes: a first quantity information 101 generated by the first quantity recording unit 12, a voltage recording information 102 generated by the voltage recording unit 13, a first temperature and humidity information 103 generated by the first temperature and humidity recording unit 14, a first time information 104 generated by the first time recording unit 15, and a first barcode information 105 generated by the first barcode scanning unit 16. Moreover, the first human-machine controller 11 is configured to allow an on-site operator of the slaughter line to input a slaughter line instruction (not shown) and simultaneously display the first quantity information 101, the voltage recording information 102, the first temperature and humidity information 103, the first time information 104, and the first barcode information 105. Further, the first time recording unit 15 is configured with at least one temperature sensor and a humidity sensor in the production working environment, and the automatic control rule of the intelligent central monitoring server instantly issues an instruction to an on-site thermostat for intelligent regulation, and a central monitoring instruction may also be issued via the human-machine interface in the backend to effectively perform remote control.

In an embodiment of the invention, the first quantity recording unit 12 is a counter that may be configured in a hanging machine; the voltage recording unit 13 is a voltmeter that may be disposed in a corona machine; the first temperature and humidity recording unit 14 is a temperature and humidity meter that may be disposed in one of a scalding machine, a glue applicator, and a cooling tank; and the first time recording unit 15 is a timer that may be disposed in one of a corona machine, a scalding machine, a hair removal machine, and a cooling bath.

The processing line monitoring module 20 is connected to the slaughter line monitoring module 10, and the processing line monitoring module 20 includes a second human-machine controller 21, a second quantity recording unit 22, and a second temperature and humidity recording unit 23, a second time recording unit 24, a metal detecting unit 25, and a second barcode scanning unit 26, wherein the second human-machine controller 21 is configured to input a processing line instruction (not shown) and is respectively connected to the second quantity recording unit 22, the voltage recording unit 23, the second temperature and humidity recording unit 24, the second time recording unit 25, and the second barcode scanning unit 26. In an embodiment of the invention, the processing line monitoring module 20 records a second monitoring information 200. The second monitoring information 200 includes: a second quantity information 201 generated by the second quantity recording unit 22, a second temperature and humidity information 202 generated by the second temperature and humidity recording unit 23, a second time information 203 generated by the second time recording unit 24, a metal detection information 204 generated by the metal detecting unit 25, and a second barcode information 205 generated by the second barcode scanning unit 26. Moreover, the second human-machine controller 21 is configured to allow on-site personnel of the processing line to input a processing line instruction (not shown) and simultaneously display the second quantity information 201, the second temperature and humidity information 202, the second time information 203, the metal detection information 204, and the second barcode information 205.

In the embodiment, the second quantity recording unit 22 is a counter that may be disposed in one of a check area and a vacuum packaging area; the second temperature and humidity recording unit 23 is a temperature and humidity meter that may be disposed in one of a freezer, a rapid freezer, a braised pot, a cooling tank, a sterilization tank, and an ice water tank; the second time recording unit 24 is a timer that may be disposed in one of a sterilization tank, a cold water tank, and a rapid freezer, and is automatically stored in a database 34 via the processing unit 35, and the personnel may query history trend graphs or tabular data via the human-machine interface 40 to be exported as electronic data files, such as EXCEL, Access, etc, wherein each of the plurality of analysis materials is configured for exporting to at least one of a video wall, a desktop computer, a notebook computer, a car computer, a personal digital assistant, a tablet computer, a smart phone, a digital photo frame, and a wearable device for reading.

The intelligent central monitoring server 30 is connected to the slaughter line monitoring module 10 and the processing line monitoring module 20, and is configured for respectively storing the first monitoring information 100 generated by the slaughter line monitoring module 10 and the second monitoring information 200 generated by the processing line monitoring module 20. The intelligent central monitoring server 30 includes a registration module 31, a login module 32, a HACCP module 33, a database 34, and a processing unit 35. In particular, the registration module 31 is configured to allow at least one user (not shown) to store at least one personal information (not shown); and the login module 32 is configured to allow the at least one user to access the first monitoring information 100, the second monitoring information 200, and the HACCP module 33 according to at least one personal information. In an embodiment of the invention, the HACCP module 33 stores information related to Hazard Analysis and Critical Control Points (HACCP) and food quality control, which may be used for analyzing and understanding hazards that may occur in the food manufacturing process and identify important control points in the process to be measured at the time of food manufacture, so that the final product is free of hazards and quality non-compliance; the intelligent central monitoring server 30 displays the registration module 31 and the login module 32 in at least one webpage conforming to Internet specifications, and allows the user to input and access data via a device such as a computer, a notebook computer, a smart phone, and the like. In the embodiment, the database 34 is configured to send and receive emails of the at least one user.

The human-machine interface 40 is connected to the slaughter production line monitoring module 10, the processing line monitoring module 20, and the intelligent central monitoring server 30. The human-machine interface 40 is configured to transmit a central monitoring instruction 400 to the slaughter line monitoring module 10 and the processing line monitoring module 20 when at least one of the first monitoring information 100 and the second monitoring information 200 is determined to be abnormal for effective central management type of coordinated control. In an embodiment of the invention, the human-machine interface 40 may be remotely operated via a device such as a computer, a notebook computer, or a smart phone.

Further, a police point may be set up at each workstation on the processing line. Each intelligent central monitoring server 30 includes a processing unit 35. When the first human-machine controller 11 or the second machine controller 21 receives an on-site value of one of the police points exceeding a preset alarm limit value, the automatic control rule of the processing unit 35 in the intelligent central monitoring server 30 sends at least one email message to the designated recipient's email mailbox for alarm notification. For example, the upper limit temperature for the set alarm limit value is 10 degrees, and when the on-site measured environment or equipment temperature exceeds 10 degrees, the intelligent central monitoring server 30 sends an email message to the designated recipient's email address, and the human-machine interface 40 also instantly displays information such as the alarm occurrence time, alarm monitoring point, and processing status. The above examples are merely for the brief description of the operation method of the intelligent central monitoring server 30 and are not necessary limitations of the invention. It is worth mentioning that, because all the detection equipment adopt a food coating design resistant to high temperature/low temperature/grease, the intelligent central monitoring server 30 and the human-machine interface 40 are used to monitor the police points established on the processing line, and the upper and lower limits of the alarm limit value are set according to the industry's know how, and therefore it is possible to ensure that the meat products of the category on the processing line are maintained at an optimal state.

In addition, the alert notification may further distinguish between different levels to allow the central monitoring instruction 400 to be approved by a supervisor at a different level via the human-machine interface 40 when the designated recipient receives the alert notification. Moreover, the intelligent central monitoring server 30 may also automatically debug the central monitoring instruction 400 by a preset rule when the alarm notification is generated to exclude abnormalities of the slaughter line monitoring module 10 or the processing line monitoring module 20 to further reduce additional manpower costs. Moreover, in addition to the instant alarm notification, the intelligent central monitoring server 30 may further calculate historical abnormalities and alarms and produce a curve to determine whether the production value of each workstation is stable. When the curve fluctuation is greater than a preset condition and is too large, the intelligent central monitoring server 30 may further collect relevant information and perform data analysis to obtain auxiliary quality determination information serving as an auxiliary basis for future quality determination.

Further, each first human-machine controller 11 or second human-machine controller 21 is electrically connected to at least one electronic scale via a communication line of RS-232 or RS485 or Ethernet, and when the on-site operator does the weighing, the first human-machine controller 11 or the second human-machine controller 21 automatically accepts the weight of the electronic scale, and level classification is performed according to the internal automatic control rule, and at the same time the measured value is transmitted to the intelligent central monitoring server 30 and is then recorded to the database 34 via the processing unit 35.

Further, an access control card swiping device is installed in a specific operation area of each plant area, and the personnel need to swipe the card to open and exit the at least one work area, and the intelligent central monitoring server 30 is electrically connected to at least one card swiping device via a communication line of RS-232 or RS485 or Ethernet. The cardholder's card swiping time is recorded when the card is swiped, which is recorded to the database 34 via the processing unit 35 in the intelligent central monitoring server 30, and the working time and the total number of employees are automatically calculated and then converted into average working hours. It is worth mentioning that the intelligent central monitoring server 30 may not only obtain the immediate number of workers of each working area according to the received access control card information by monitoring the access control card swiping device, but may also directly calculate the working hours of each month and production status of each work area.

In the embodiment, the average working hours=(total number of production/total number of work personnel)/total hours (unit: quantity/per person/hour).

Further, the intelligent central monitoring server 30 has a production history tracing function, and the intelligent central monitoring server 30 is connected to at least one ERP database, and the personnel inputs a product production number such as a batch number in the human-machine interface, and the intelligent central monitoring server 30 may search for the source information of the product, such as the source farm name, the purchase quantity, the production quantity, etc. The above examples are only for the brief description of the operation method of the intelligent central monitoring server 30, and are not necessary limits of the invention. This feature may be used as a food safety and prevention management.

Specifically, regarding the history tracing function, the intelligent central monitoring server 30 may generate a history barcode according to a sequence in the ERP database to provide the first barcode scanning unit 16 and the second barcode scanning unit 26 for scanning. In this way, via the generated history barcode, starting from checking the incoming material, the workstations are automatically connected in series all the way to the last quantity/quality control system, and the control is performed via a batch management method. In addition, the starting point of each workstation may also be configured with the final number of input and output of the product line that are returned to the intelligent central monitoring server 30 for calculation of production yield.

Further, each of the first human-machine controller 11 or the second human-machine controller 21 is electrically connected to at least one metal detecting device via a communication line of RS-232 or RS485 or Ethernet. When the metal detecting device operates, the first human-machine controller 11 or the second human-machine controller 21 automatically receives the normal and abnormal quantity data detected by the metal detecting device, and the value is sent to the intelligent central monitoring server 30 via the first human-machine controller 11 or the second human-machine controller 21 and then recorded to the database 34 by the processing unit 35.

As described above, the technical content described in the invention may be applied to agricultural animal husbandry via big data analysis to improve market evaluation and performance evaluation.

Figure 1:
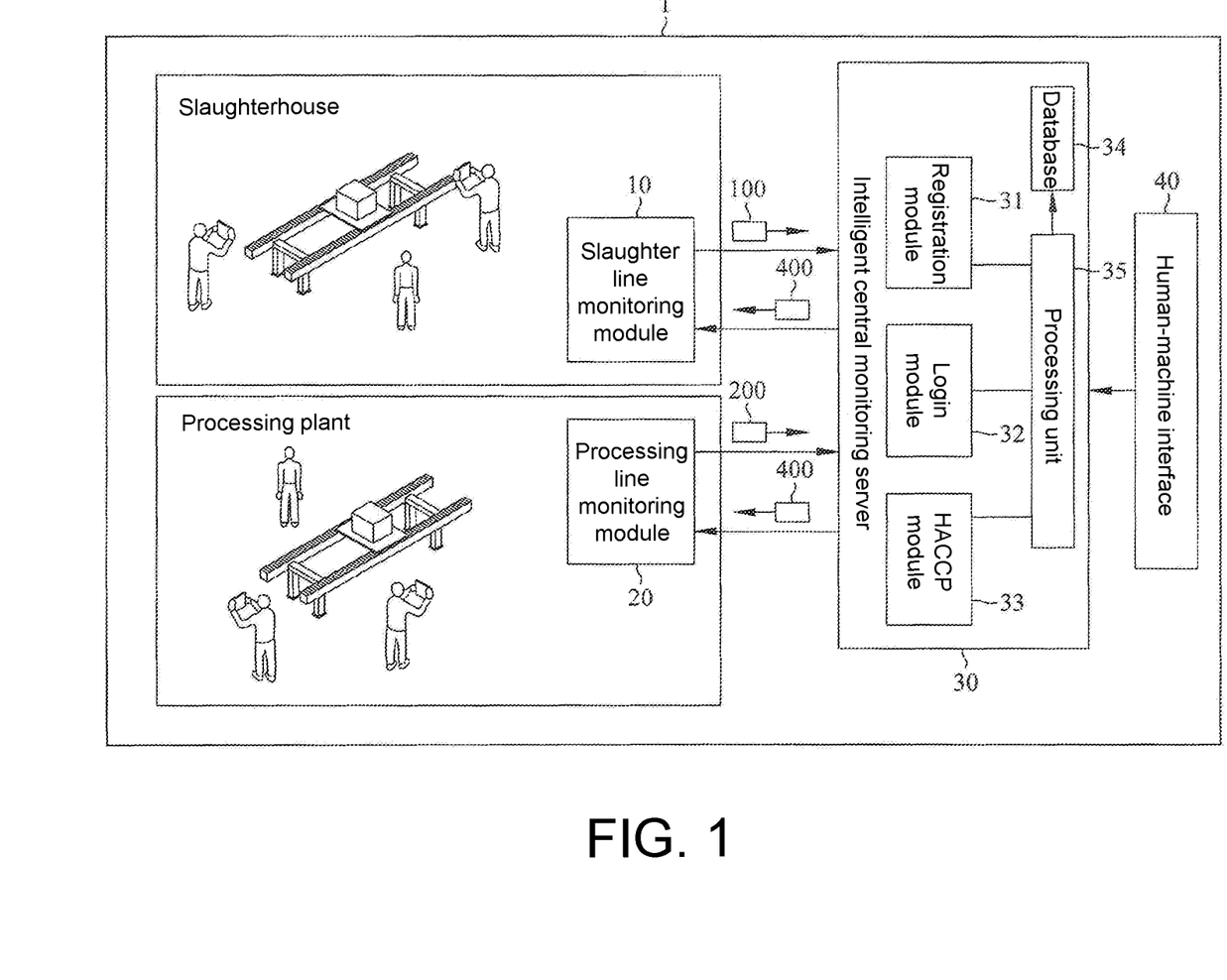
FIG. 1 to FIG. 4 are schematics of the architecture of a food safety quality and performance monitoring system of an embodiment of the invention.
Figure 2:
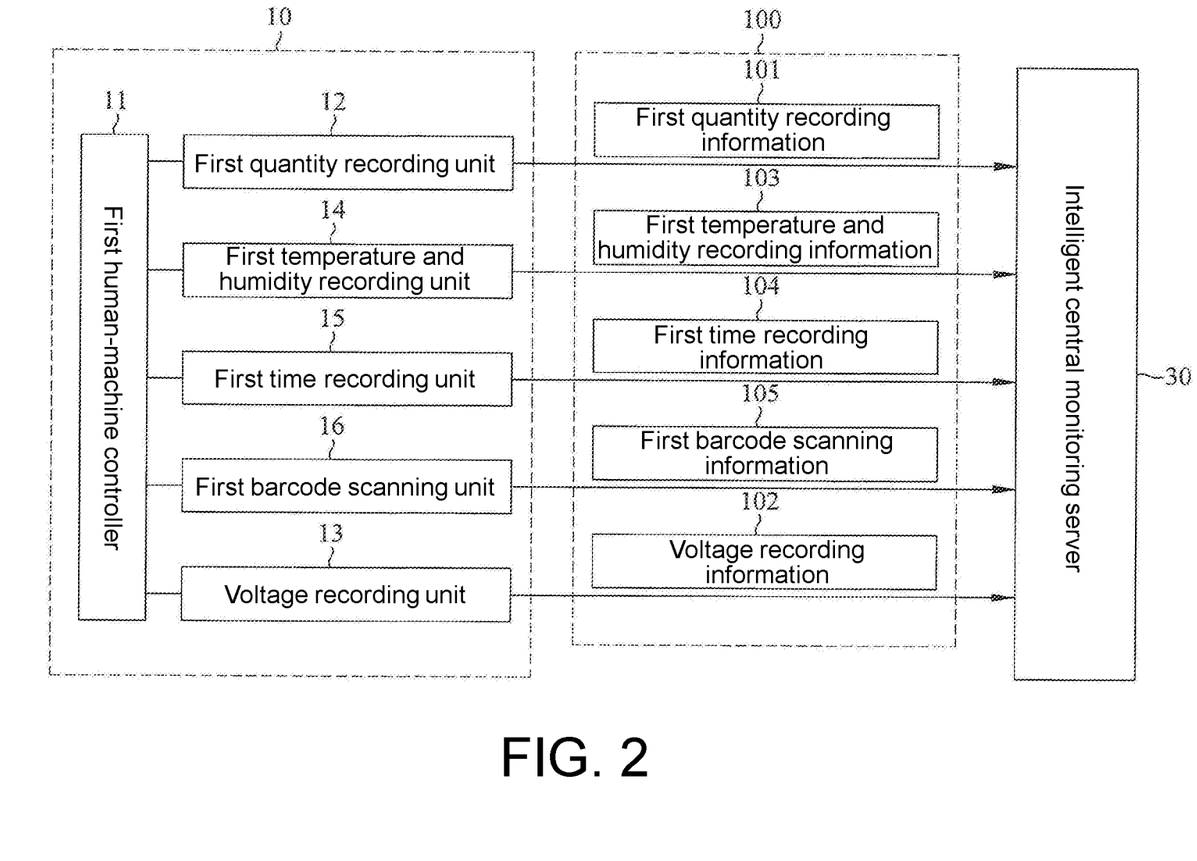
Figure 3:
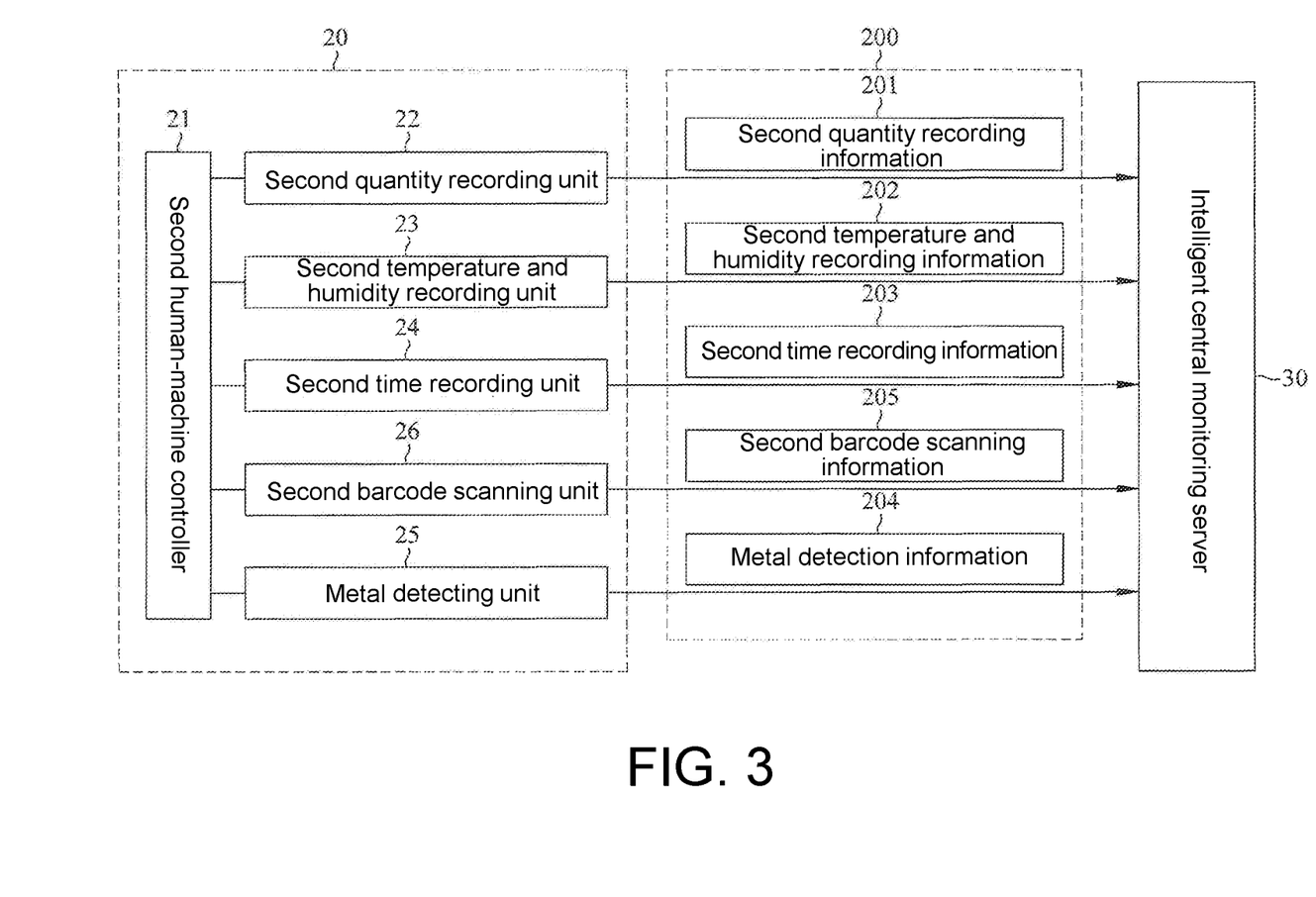
Figure 4:
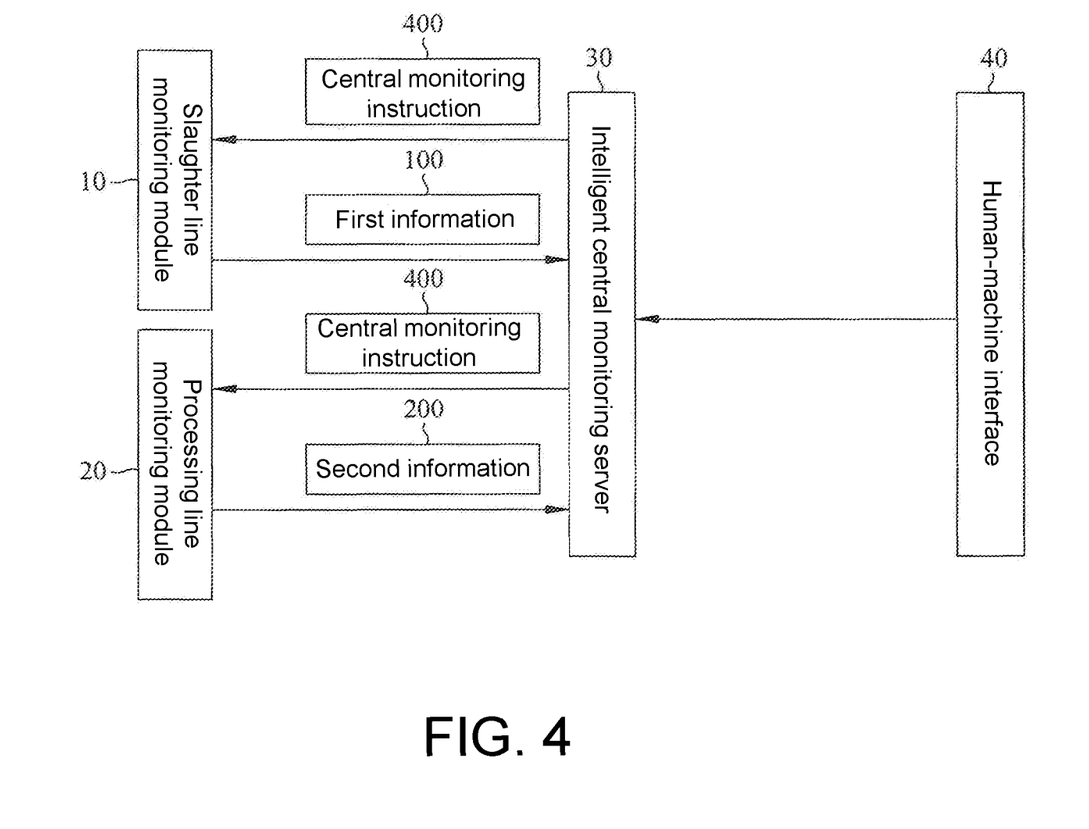
Figure 5:
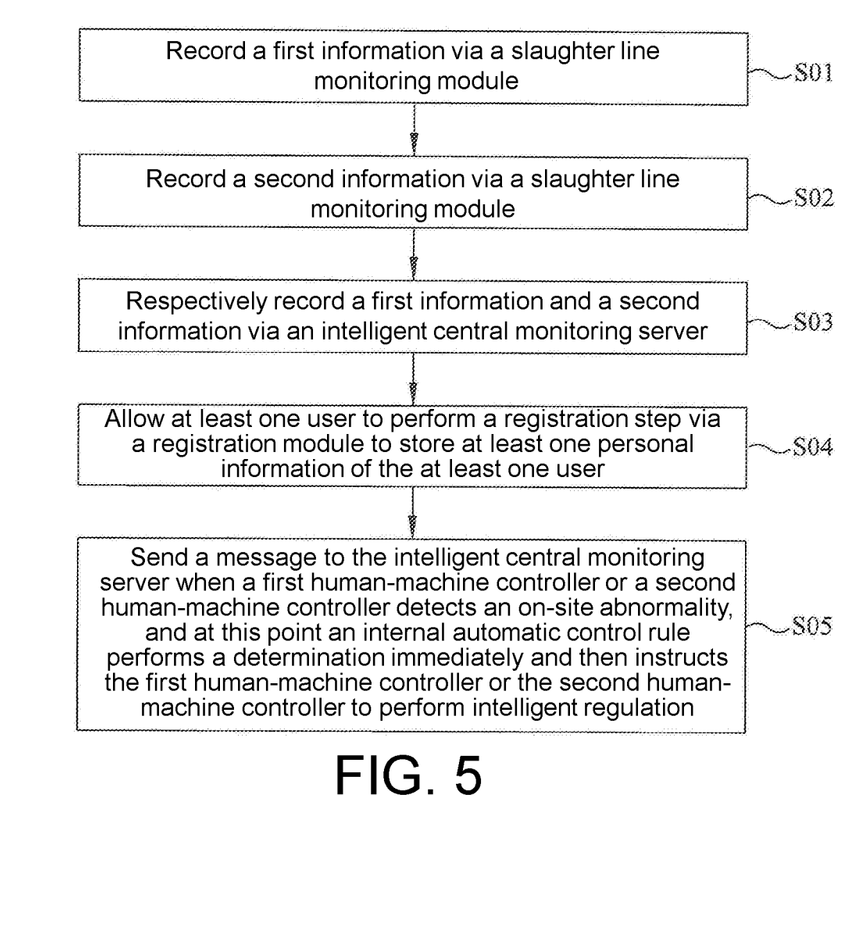
FIG. 5 is a flowchart of a method for a food safety quality and performance monitoring system of an embodiment of the invention.

When the food safety quality and performance monitoring system of the invention is started, the first monitoring information 100 is recorded via the slaughter line monitoring module 10 (step S01), and the first human-machine controller displays the first quantity information 101, the voltage recording information 102, the first temperature and humidity information 103, the first time information 104, and the first barcode information 105; then, the second monitoring information 200 is recorded via the processing line monitoring module 20 (step S02), and the second human-machine controller 21 displays the second quantity information 201, the second temperature and humidity information 202, the second time information 203, the metal detection information 204, and the second barcode information 205; then, after the intelligent central monitoring server 30 respectively stores the first monitoring information 100 and the second monitoring information 200 (step S03), the registration module 31 stores at least one personal information of at least one user by allowing the at least one user to perform a registration step (step S04); finally, at least one user who has completed the registration step may use the login module 32 to allow at least one user to access the first monitoring information 100, the second monitoring information 200, and the HACCP module 33 according to at least one personal information; in addition, when the human interface 40 determines that at least one of the first monitoring information 100 and the second monitoring information 200 is abnormal, the central monitoring instruction 400 is transmitted to the slaughter line monitoring module 10 and the processing line monitoring module 20 (step S05) to perform an effective central management type of coordinated control. The at least one personal information is used as a combination of market product demand analysis and evaluation of capacity usage.

In this way, both the slaughter line and the processing line have their own independent and automatic operation of a plurality of monitoring modules, which may make important information of a plurality of monitoring and control points including time, temperature and humidity, quantity, etc. in the production process to be automatically recorded, and the first human-machine controller and the second human-machine controller may instantly display the current state and realize warning function to prevent problematic products from reaching the production backend or even the consumer; moreover, in the later stage, whether there is any doubt in the slaughtering or processing flow in the production line, the owner or the at least one user may further learn all relevant information about food safety quality via the intelligent central monitoring server 30 storing the first monitoring information and the second monitoring information, and the owner may also further learn whether the performance on the production process is low or abnormal respectively via the first monitoring information 100 displayed by the first human-machine controller 11 on the slaughter line and the second monitoring information 200 displayed by the second human-machine controller 21 on the processing line, and the human-machine interface 40 in the backend may issue the central monitoring instruction 400 to effectively perform central management type of coordinated control to perform abnormal processing to reduce and prevent production losses to achieve the objectives of maintaining consumer food safety and improving the production efficiency of the industry.

Although embodiments are described with reference to the many exemplary embodiments of the application, those skilled in the art may think of a plurality of other modifications and embodiments, and these modifications and embodiments are within the spirit and scope of the disclosure principle. In particular, various changes and modifications may be made for the components and/or arrangements combined and configured for the subject within the scope of the present disclosure, figures, and attached claims. Alternative uses will be apparent to those skilled in the art in addition to variations and modifications in the components and/or arrangements.

What is claimed is:

1. A food safety quality and performance monitoring system, comprising:

a slaughter line monitoring module configured to generate a first monitoring information, comprising a first human-machine controller, at least one first quantity recording unit, at least one voltage recording unit, at least one first temperature and humidity recording unit, at least one first time recording unit, and at least one first barcode scanning unit, wherein the first human-machine controller is configured to input a slaughter line instruction and is respectively connected to the at least one first quantity recording unit, the at least one voltage recording unit, the at least one first temperature and humidity recording unit, the at least one first time recording unit, and the at least one first barcode scanning unit;

a processing line monitoring module configured to generate a second monitoring information and connected to the slaughter line monitoring module, wherein the processing line monitoring module comprises a second human-machine controller, at least one second quantity recording unit, at least one second temperature and humidity recording unit, at least one second time recording unit, at least one metal detecting unit, and at least one second barcode scanning unit, wherein the second human-machine controller is configured to input a processing line instruction and is respectively connected to the at least one second quantity recording unit, the at least one voltage recording unit, the at least one second temperature and humidity recording unit, the at least one second time recording unit, and the at least one second barcode scanning unit;

an intelligent central monitoring server connected to the slaughter line monitoring module and the processing line monitoring module and configured to respectively store the first monitoring information and the second monitoring information; the intelligent central monitoring server comprises a registration module, a login module, and an HACCP module, wherein the registration module is configured to allow at least one user to store at least one personal information; and the login module is configured to allow the at least one user to access the first monitoring information, the second monitoring information, and the HACCP module according to the at least one personal information; and a human-machine interface connected to the slaughter line monitoring module, the processing line monitoring module, and the intelligent central monitoring server to receive the first monitoring information and the second monitoring information, wherein when the human-machine interface determines at least one of the first monitoring information and the second monitoring information is abnormal, a central monitoring instruction is transmitted to the abnormal slaughter line monitoring module or the processing line monitoring module.

2. The food safety quality and performance monitoring system according to claim 1, wherein a webpage module further comprises a database and a processing unit; each of the at least one voltage recording unit is a voltmeter disposed in a corona machine; and the at least one personal information is used as a combination of a market product demand analysis and an evaluation of a production usage.

3. The food safety quality and performance monitoring system according to claim 1, wherein each of the at least one first quantity recording unit is a counter disposed in a hanging machine; and each of the at least one second quantity recording unit is a counter disposed in one of a check area and a vacuum packaging area.

4. The food safety quality and performance monitoring system according to claim 1, wherein each of the at least one first temperature and humidity recording unit is a temperature and humidity meter disposed in one of a scalding machine, a glue applicator, and a cooling tank; and each of the at least one second temperature and humidity recording unit is a temperature and humidity meter disposed in one of a freezer, a rapid freezer, a braised pot, a cooling tank, a sterilization tank, and an ice water tank.

5. The food safety quality and performance monitoring system of claim 1, wherein each of the at least one first time recording unit is a timer disposed in one of a corona machine, a scalding machine, a hair removal machine, and a cooling tank; and each of the at least one second time recording unit is a timer disposed in one of a sterilization tank, a cold water tank, and a rapid freezer.

6. The food safety quality and performance monitoring system according to claim 1, wherein the intelligent central monitoring server further receives an access control card information to obtain an immediate number of workers of each working area according to the access control card information and statistically calculate monthly working hours and a production status of each of the working areas.

7. The food safety quality and performance monitoring system according to claim 1, wherein the intelligent central monitoring server further generates a history barcode to be scanned by the at least one first barcode scanning unit and the at least one second barcode scanning unit to perform a batch management.

8. The food safety quality and performance monitoring system according to claim 1, wherein the intelligent central monitoring server automatically debugs the central monitoring instruction via a preset rule to exclude an abnormality of the slaughter line monitoring module or the processing line monitoring module.

9. The food safety quality and performance monitoring system according to claim 1, wherein the intelligent central monitoring server further counts the abnormality of a history and draws a curve according to the abnormality of the history, when a fluctuation of the curve is greater than a preset condition, the intelligent central monitoring server analyzes an auxiliary quality determination information.

10. A food safety quality and performance monitoring method, comprising the following steps:

recording a first monitoring information via a slaughter line monitoring module, the first monitoring information comprising: at least one first quantity information, at least one voltage recording information, at least one first temperature and humidity information, at least one first time information, and at least one first barcode information; and a first human-machine controller is configured to input a slaughter line instruction and simultaneously display at least one of the at least one first quantity information, the at least one voltage recording information, the at least one first temperature and humidity information, the at least one first time information, and the at least one first barcode information;

recording a second monitoring information via a processing line monitoring module, the second monitoring information comprising: at least one second quantity information, at least one second temperature and humidity information, at least one second time information, at least one metal detection information, and at least one second barcode information; and a second human-machine controller is configured to input a processing line instruction and simultaneously display the at least one second quantity information, the at least one second temperature and humidity information, the at least one second time information, the at least one metal detection information, and the at least one second barcode information;

respectively storing a first monitoring information generated by the slaughter line monitoring module and a second monitoring information generated by the processing line monitoring module via an intelligent central monitoring server;

storing at least one personal information of at least one user via a registration module comprised in the intelligent central monitoring server;

allowing the at least one user to access the first monitoring information, the second monitoring information, and an HACCP module comprised in webpage information via a login module comprised in the intelligent central monitoring server according to the at least one personal information; and transmitting a central monitoring instruction to the slaughter line monitoring module and the processing line monitoring module when at least one of the first monitoring information and the second monitoring information is determined to be abnormal.

11. The food safety quality and performance monitoring method according to claim 10, wherein the webpage module further comprises a database and a processing unit; and each of at least one voltage recording unit for recording the at least one voltage information is a voltmeter disposed in a corona machine.

12. The food safety quality and performance monitoring method according to claim 10, wherein each of at least one first quantity recording unit for recording the at least one first quantity information is a counter disposed in a hanging machine; and each of at least one second quantity recording unit for recording the at least one second quantity is a counter disposed in one of a check area and a vacuum packaging area.

13. The food safety quality and performance monitoring method according to claim 10, wherein each of at least one first temperature and humidity recording unit for recording the at least one first temperature and humidity information is a temperature and humidity meter disposed in one of a scalding machine, a glue applicator, and a cooling tank; and each of at least one second temperature and humidity recording unit for recording the at least one second temperature and humidity information is a temperature and humidity meter disposed in one of a freezer, a rapid freezer, a braised pot, a cooling tank, a sterilization tank, and an ice water tank.

14. The food safety quality and performance monitoring method according to claim 10, wherein each of at least one time recording unit for recording the at least one first time information is a timer disposed in one of a corona machine, a scalding machine, a hair removal machine, and a cooling tank; and each of the at least one second time recording unit is a timer disposed in one of a sterilization tank, a cold water tank, and a rapid freezer.

* * * * *